United States Patent [19]
Cavalla et al.

[11] Patent Number: 6,037,470
[45] Date of Patent: Mar. 14, 2000

[54] PURINE COMPOUNDS HAVING PDE IV INHIBITORY ACTIVITY AND METHODS OF SYNTHESIS

[75] Inventors: David J. Cavalla, Cambridge, United Kingdom; Mark Chasin, Manalapan, N.J.; Peter Hofer, Liestal, Switzerland

[73] Assignee: Euro-Celtique S.A., Luxembourg

[21] Appl. No.: 09/209,658

[22] Filed: Dec. 10, 1998

Related U.S. Application Data

[60] Provisional application No. 60/069,371, Dec. 12, 1997.

[51] Int. Cl.[7] .................. C07D 473/34; C07D 473/30; C07D 473/22; C07D 239/56

[52] U.S. Cl. .................. 544/277; 544/256; 544/267; 544/271; 544/272; 544/311; 544/312

[58] Field of Search .......................................... 544/277

[56] References Cited

FOREIGN PATENT DOCUMENTS

95/00516  1/1995  WIPO .

OTHER PUBLICATIONS

*Some New N–Methylpurines*, Gertrude B. Elion, CIBA foundation Symp. Chem Biol. Purines, 1957, pp. 39–49.

Selective Type IV Phosphodiesterase Inhibitors as Antiasthmatic Agents. The Synthesis and Biological Activities of 3–(Cyclopentyloxy)–4–methoxybenzamides and Analogues, Michael J. Ashton, et al., Journal of Medicinal Chemistry, 1994, vol. 37, No. 11, pp. 1696–1703.

Synthesis of 3–Methylisoguanine [6–Amino–3–methylpurin–2(3H)–one], G.T. Rogers and T.L.B. Ulbricht, J. Chemical Soc.(C), 1971, pp. 2364–2366.

Synthesis of Potential Anticancer Agents. XIX. 2–Substituted N[6]–Alkyladeninse, John A. Montgomery, Lee B. Holum and Thomas P. Johnston, The Kettering–Meyer Laboratory, Southern Research Institute, Aug. 5, 1959, vol. S. pp. 3963–3967.

*Primary Examiner*—Mark L. Berch
*Attorney, Agent, or Firm*—Davidson, Davidson & Kappel, LLC

[57] ABSTRACT

The present invention comprises a method of synthesizing compounds of formula (I):

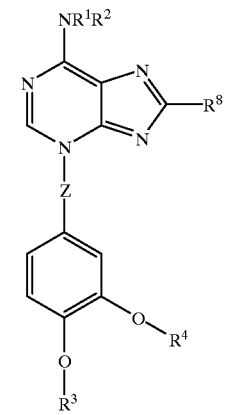

wherein Z, $R^1$, $R^2$, $R^3$, $R^4$ and $R^8$ are as described herein; comprising the steps of.

(a) reacting a compound of the formula (II)

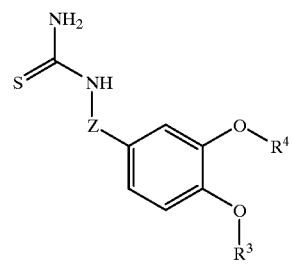

with an effective amount of ethyl cyanoacetate to form a compound of the formula (III)

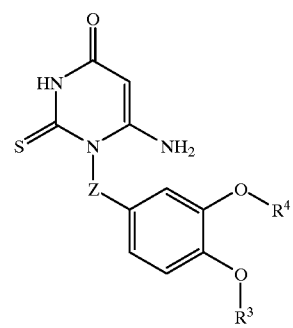

(b) subjecting said compound (III) to successive steps of nitrosating with a nitrosating agent to form a nitro group [amination], reduction of the nitro group to an amine group with a reducing agent, and [amidation] acylation of the amine group to an amide group with an acylating agent, to form compound (IV)

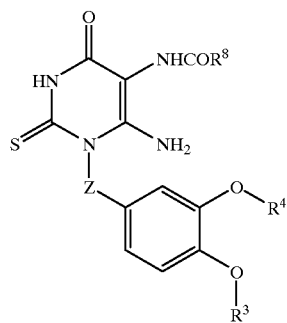

(IV)

(c) reacting said compound (IV) with an effective amount of a base to form compound (V)

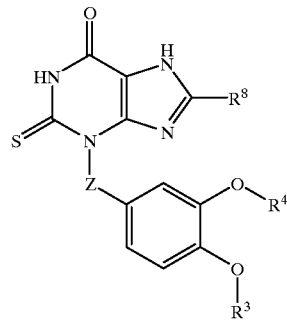

(V)

(d) reacting said compound (V) with an effective amount of a desulfurization compound to form compound (VI)

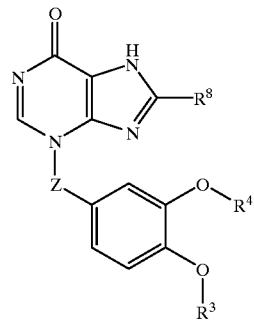

(VI)

and (e) subjecting said oxo group of compound (VI) to the successive steps of halogenation with a halogenating agent and displacement with an amine of the formula $NR^1R^2$, wherein $R^1$ and $R^2$ are as defined above, to form said compound of formula 1.

15 Claims, No Drawings

PURINE COMPOUNDS HAVING PDE IV INHIBITORY ACTIVITY AND METHODS OF SYNTHESIS

This application is a continuation-in-part of provisional application Ser. No. 60/069,371, filed Dec. 12, 1997.

BACKGROUND OF THE INVENTION

Asthma is a complex disease involving the concerted actions of multiple inflammatory and immune cells, spasmogens, inflammatory mediators, cytokines and growth factors. In recent practice there have been four major classes of compounds used in the treatment of asthma, namely bronchodilators (e.g., β-adrenoceptor agonists), anti-inflammatory agents (e.g., corticosteroids), prophylactic anti-allergic agents (e.g., cromolyn sodium) and xanthines (e.g., theophylline) which appear to possess both bronchodilating and anti-inflammatory activity.

Theophylline has been a preferred drug of first choice in the treatment of asthma. Although it has been touted for its direct bronchodilatory action, theophylline's therapeutic value is now believed to also stem from anti-inflammatory activity. Its mechanism of action remains unclear. However, it is believed that several of its cellular activities are important in its activity as an anti-asthmatic, including cyclic nucleotide phosphodiesterase inhibition, adenosine receptor antagonism, stimulation of catecholamine release, and its ability to increase the number and activity of suppressor T-lymphocytes. While all of these may actually contribute to its activity, only PDE inhibition may account for both the anti-inflammatory and bronchodilatory components. However, theophylline is known to have a narrow therapeutic index and a wide range of untoward side effects which are considered problematic.

Of the activities mentioned above, theophylline's activity in inhibiting cyclic nucleotide phosphodiesterase has received considerable attention recently. Cyclic nucleotide phosphodiesterases (PDEs) have received considerable attention as molecular targets for anti-asthmatic agents. Cyclic 3',5'-adenosine monophosphate (cAMP) and cyclic 3',5'-guanosine monophosphate (cGMP) are known second messengers that mediate the functional responses of cells to a multitude of hormones, neurotransmitters and autocoids. At least two therapeutically important effects could result from phosphodiesterase inhibition, and the consequent rise in intracellular adenosine 3',5'-monophosphate (cAMP) or guanosine 3',5'-mono-phosphate (cGMP) in key cells in the pathophysiology of asthma. These are smooth muscle relaxation (resulting in bronchodilation) and anti-inflammatory activity.

It has become known that there are multiple, distinct PDE isoenzymes which differ in their cellular distribution. A variety of inhibitors possessing a marked degree of selectivity for one isoenzyme or the other have been synthesized.

The structure-activity relationships (SAR) of isozyme-selective inhibitors has been discussed in detail, e.g., in the article of Theodore J. Torphy, et al., "Novel Phosphodiesterase Inhibitors For The Therapy Of Asthma", Drug News & Prospectives, 6(4) May 1993, pages 203–214. The PDE enzymes can be grouped into five families according to their specificity toward hydrolysis of cAMP or cGMP, their sensitivity to regulation by calcium, calmodulin or cGMP, and their selective inhibition by various compounds. PDE I is stimulated by $Ca^{2+}$/calmodulin. PDE II is cGMP-stimulated, and is found in the heart and adrenals. PDE III is cGMP-inhibited, and inhibition of this enzyme creates positive inotropic activity. PDE IV is cAMP specific, and its inhibition causes airway relaxation, antiinflammatory and antidepressant activity. PDE V appears to be important in regulating cGMP content in vascular smooth muscle, and therefore PDE V inhibitors may have cardiovascular activity.

While there are compounds derived from numerous structure activity relationship studies which provide PDE III inhibition, the number of structural classes of PDE IV inhibitors is relatively limited. Analogues of rolipram, which has the following structural formula (A):

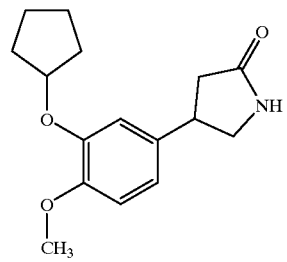

and of RO-20-1724, which has the following structural formula (B):

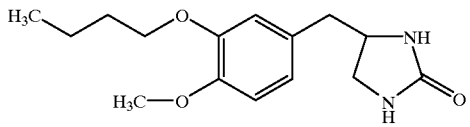

have been studied.

U.S. Pat. No. 4,308,278 discloses compounds of the formula (C)

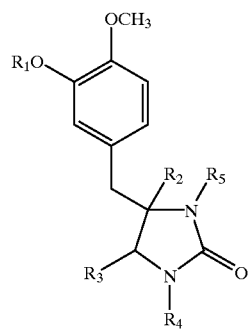

wherein $R_1$ is ($C_3$–$C_6$) cycloalkyl or benzyl; each of $R_2$ and $R_3$ is hydrogen or ($C_1$–$C_4$) alkyl; $R_4$ is $R_2$ or alkoxycarbonyl; and $R_5$ is hydrogen or alkoxycarbonyl.

Compounds of Formula (D) are disclosed in U.S. Pat. No. 3,636,039. These compounds are benzylimidazolidinones which act as hypertensive agents.

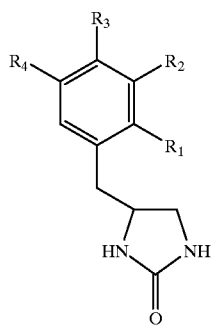

Substituents $R_1$–$R_4$ in Formula D represent a variety of groups, including hydrogen and lower alkyl.

PCT publication WO 87/06576 discloses antidepressants of Formula E:

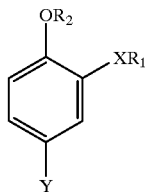

wherein $R_1$ is a polycycloalkyl group having from 7 to 11 carbon atoms; $R_2$ is methyl or ethyl; X is O or NH; and Y comprises a mono-or bicyclic heterocyclic group with optional substituents.

Rolipram, which was initially studied because of its activity as an anti-depressant, has been shown to selectively inhibit the PDE IV enzyme and this compound has since become a standard agent in the classification of PDE enzyme subtypes. There appears to be considerable therapeutic potential for PDE IV inhibitors. Early work focused on depression as a CNS therapeutic endpoint and on inflammation, and has subsequently been extended to include related diseases such as dementia, including vascular dementia, multi-in-farct dementia and Alzheimer's Disease, and asthma. In-vitro, rolipram, RO20-1724 and other PDE IV inhibitors have been shown to inhibit (1) mediator synthesis/release in mast cells, basophils, monocytes and eosinophils; (2) respiratory burst, chemotaxis and degranulation in neutrophils and eosinophils; and (3) mitogen-dependent growth and differentiation in lymphocytes (The PDE IV Family Of Calcium-Phosphodiesterases Enzymes, John A. Lowe, III, et al., Drugs of the Future 1992, 17(9):799–807).

PDE IV is present in all the major inflammatory cells in asthma including eosinophils, neutrophils, T-lymphocytes, macrophages and endothelial cells. Its inhibition causes down regulation of inflammatory cell activation and relaxes smooth muscle cells in the trachea and bronchus. On the other hand, inhibition of PDE III, which is present in myocardium, causes an increase in both the force and rate of cardiac contractility. These are undesirable side effects for an anti-inflammatory agent. Theophylline, a non-selective PDE inhibitor, inhibits both PDE III and PDE IV, resulting in both desirable anti-asthmatic effects and undesirable cardiovascular stimulation. With this well-known distinction between PDE isozymes, the opportunity for concomitant anti-inflammation and bronchodilation without many of the side effects associated with theophylline therapy is apparent.

The increased incidence of morbidity and mortality due to asthma in many Western countries over the last decade has focused the clinical emphasis on the inflammatory nature of this disease and the benefit of inhaled steroids. Development of an agent that possesses both bronchodilatory and antiinflammatory properties would be most advantageous.

It appears that selective PDE IV inhibitors should be more effective with fewer side effects than theophylline. Clinical support has been shown for this hypothesis. Furthermore, it would be desirable to provide PDE IV inhibitors which are more potent and selective than rolipram and therefore have a lower $IC_{50}$ so as to reduce the amount of the agent required to effect PDE IV inhibition.

OBJECTS AND SUMMARY OF THE INVENTION

It is accordingly a primary object of the present invention to provide new compounds which are more effective selective PDE IV inhibitors than known prior art compounds.

It is another object of the present invention to provide new compounds which act as effective PDE IV inhibitors with lower PDE III inhibition.

It is another object of the present invention to provide methods for treating a patient requiring PDE IV inhibition.

It is another object of the present invention to provide new compounds for treating disease states associated with abnormally high physiological levels of inflammatory cytokines, including tumor necrosis factor.

It is another object of the present invention to provide a method of synthesizing the new compounds of this invention.

It is another object of the present invention to provide a method for treating a patient suffering from disease states such as asthma, allergies, inflammation, depression, dementia, including vascular dementia, multi-in-farct dementia, and Alzheimer's Disease, a disease caused by Human Immunodeficiency Virus and disease states associated with abnormally high physiological levels of inflammatory cytokines.

Other objects and advantages of the present invention will become apparent from the following detailed description thereof.

With the above and other objects in view, the present invention comprises compounds having the general formula (I):

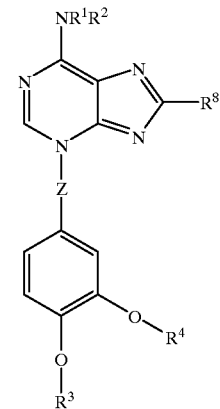

wherein:

Z is selected from the group consisting of alkylene groups such as $CH_2$, $CH_2CH_2$, $CH(CH_3)$; alkenylene groups such as $CH=CH$; alkynylene groups such as $C\equiv C$; and NH, $N(C_1-C_3$ alkyl), O, S, $C(O)CH_2$ and $OCH_2$;

benefit from a modification of PDE IV enzyme activities in their bodies.

The invention also comprises methods of making compounds of formula (I), according to a five step synthetic scheme as generally set forth below:

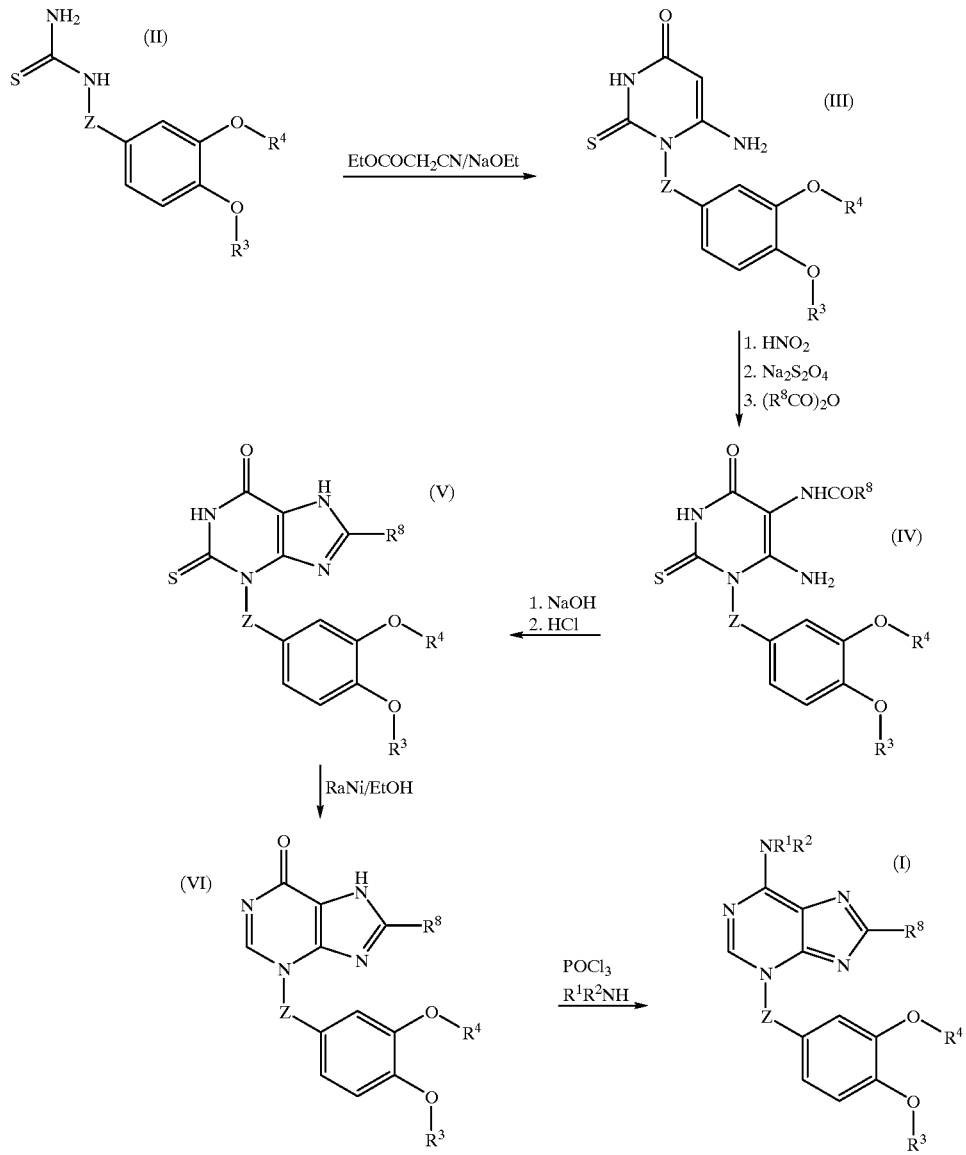

$R^1$ and $R^2$ are independently selected from the group consisting of hydrogen and a $C_1-C_8$ straight or branched alkyl or $C_3-C_8$ cycloalkyl;

$R^3$ is a $C_1-C_{12}$ straight or branched alkyl;

$R^4$ is a $C_3-C_{10}$ cycloalkyl optionally substituted with OH, or a $C_3-C_{10}$ cycloalkenyl optionally substituted with OH, and $R^8$ is a $C_1-C_8$ straight or branched alkyl or a $C_3-C_8$ cycloalkyl, optionally substituted with OH.

The present invention is also related to methods of using compounds of formula (I) for treating patients who can The invention is also related to a method of treating mammals with the above compounds.

DETAILED DESCRIPTION OF THE INVENTION

The present invention is directed to compounds having the general formula (I):

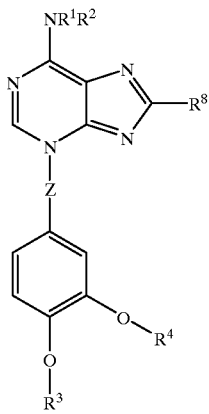

wherein:

Z is selected from the group consisting of alkylene groups such as $CH_2$, $CH_2CH_2$, $CH(CH_3)$, alkenylene groups such as $CH=CH$; alkynylene groups such as $C\equiv C$; and NH, $N(C_1-C_3$ alkyl), O, S, $C(O)CH_2$ and $OCH_2$;

$R^1$ and $R^2$ are independently selected from the group consisting of hydrogen and a $C_1-C_8$ straight or branched alkyl or $C_3-C_8$ cycloalkyl;

$R^3$ is a $C_1-C_{12}$ straight or branched alkyl;

$R^4$ is a $C_3-C_{10}$ cycloalkyl optionally substituted with OH, or a $C_3-C_{10}$ cylcoalkenyl optionally substituted with OH; and $R^8$ is a $C_1-C_8$ straight or branched alkyl or a $C_3-C_8$ cycloalkyl, optionally substituted with OH.

As used herein, the following terms are intended to have the meaning as understood by persons of ordinary skill in the art, and are specifically intended to include the meanings set forth below:

"Alkyl" means a linear or branched aliphatic hydrocarbon group having a single radical. Examples of alkyl groups include methyl, propyl, isopropyl, butyl, n-butyl, isobutyl, sec-butyl, tert-butyl, pentyl, hexyl, heptyl, cetyl, and the like. A branched alkyl means that one or more alkyl groups such as methyl, ethyl or propyl are attached to a linear alkyl chain.

The term "cycloalkyl" means a non-aromatic mono- or multicyclic ring system having a single radical. Exemplary monocyclic cycloalkyl rings include cyclopentyl, cyclohexyl and cycloheptyl. Exemplary multicylic cycloalkyl rings include adamantyl and norbornyl.

The term "cycloalkenyl" means a non-aromatic monocyclic or multicyclic ring system containing a carbon-carbon double bond and having a single radical. Exemplary monocyclic cycloalkenyl rings include cyclopentenyl, cyclohexenyl or cycloheptenyl. An exemplary multicyclic cycloalkenyl ring is norbornenyl. "Alkylene" means a linear or branched aliphatic hydrocarbon group having two radicals. Examples of alkylene groups include methylene, propylene, isopropylene, butylene, and the like.

The term "alkenylene" means a linear or branched aliphatic hydrocarbon group containing a carbon-carbon double bond, having two radicals.

The term "alkynylene" means a linear or branched aliphatic hydrocarbon group containing a carbon-carbon triple bond and, having two radicals.

"Alkoxy" means an alkyl-O-group in which the alkyl group is as previously described. Exemplary alkoxy groups include methoxy, ethoxy, n-propoxy, i-propoxy, n-butoxy and heptoxy.

The term "cycloalkoxy" means a cycloalkyl-O-group in which the cycloalkyl group is as previously described. Exemplary cycloalkoxy groups include cyclopentyloxy.

As used herein, the term "patient" includes both human and other mammals.

The present invention also includes organic and inorganic salts, hydrates, esters, prodrugs and metabolites of the compounds of formula I.

The compounds of the present invention can be administered to anyone requiring PDE IV inhibition. Administration may be orally, topically, by suppository, inhalation or insufflation, or parenterally.

The present invention also encompasses all pharmaceutically acceptable salts of the foregoing compounds. One skilled in the art will recognize that acid addition salts of the presently claimed compounds may be prepared by reaction of the compounds with the appropriate acid via a variety of known methods. Alternatively, alkali and alkaline earth metal salts are prepared by reaction of the compounds of the invention with the appropriate base via a variety of known methods. For example, the sodium salt of the compounds of the invention can be prepared via reacting the compound with sodium hydride.

Various oral dosage forms can be used, including such solid forms as tablets, gelcaps, capsules, caplets, granules, lozenges and bulk powders and liquid forms such as emulsions, solutions and suspensions. The compounds of the present invention can be administered alone or can be combined with various pharmaceutically acceptable carriers and excipients known to those skilled in the art, including but not limited to diluents, suspending agents, solubilizers, binders, retardants, disintegrants, preservatives, coloring agents, lubricants and the like.

When the compounds of the present invention are incorporated into oral tablets, such tablets can be compressed, tablet triturates, enteric-coated, sugar-coated, film-coated, multiply compressed or multiply layered. Liquid oral dosage forms include aqueous and nonaqueous solutions, emulsions, suspensions, and solutions and/or suspensions reconstituted from non-effervescent granules, containing suitable solvents, preservatives, emulsifying agents, suspending agents, diluents, sweeteners, coloring agents, and flavorings agents. When the compounds of the present invention are to be injected parenterally, they may be, e.g., in the form of an isotonic sterile solution. Alternatively, when the compounds of the present invention are to be inhaled, they may be formulated into a dry aerosol or may be formulated into an aqueous or partially aqueous solution.

In addition, when the compounds of the present invention are incorporated into oral dosage forms, it is contemplated that such dosage forms may provide an immediate release of the compound in the gastrointestinal tract, or alternatively may provide a controlled and/or sustained release through the gastrointestinal tract. A wide variety of controlled and/or sustained release formulations are well known to those skilled in the art, and are contemplated for use in connection with the formulations of the present invention. The controlled and/or sustained release may be provided by, e.g., a coating on the oral dosage form or by incorporating the compound(s) of the invention into a controlled and/or sustained release matrix.

Specific examples of pharmaceutically acceptable carriers and excipients that may be used to formulate oral dosage forms, are described in the *Handbook of Pharmaceutical Excipients,* American Pharmaceutical Association (1986), incorporated by reference herein. Techniques and compositions for making solid oral dosage forms are described in

*Pharmaceutical Dosage Forms: Tablets* (Lieberman, Lachman and Schwartz, editors) 2nd edition, published by Marcel Dekker, Inc., incorporated by reference herein. Techniques and compositions for making tablets (compressed and molded), capsules (hard and soft gelatin) and pills are also described in *Remington's Pharmaceutical Sciences* (Arthur Osol, editor), 1553–1593 (1980), incorporated herein by reference. Techniques and composition for making liquid oral dosage forms are described in *Pharmaceutical Dosage Forms: Disperse Systems,* (Lieberman, Rieger and Banker, editors) published by Marcel Dekker, Inc., incorporated herein by reference.

When the compounds of the present invention are incorporated for parenteral administration by injection (e.g., continuous infusion or bolus injection), the formulation for parenteral administration may be in the form of suspensions, solutions, emulsions in oily or aqueous vehicles, and such formulations may further comprise pharmaceutically necessary additives such as stabilizing agents, suspending agents, dispersing agents, and the like. The compounds of the invention may also be in the form of a powder for reconstitution as an injectable formulation.

The dose of the compounds of the present invention is dependent upon the affliction to be treated, the severity of the symptoms, the route of administration, the frequency of the dosage interval, the presence of any deleterious side-effects, and the particular compound utilized, among other things.

DETAILED DESCRIPTION OF PREFERRED EMBODIMENTS

As used herein, the term "Et" refers to any ethyl group, and the term "Bu" refers to a butyl group. "Bu$^t$" refers to a tertiary butyl group. The term "THF" refers to tetrohydrofuran. The term "DMAC" refers to dimethyl acetate. The term "Ph" refers to a phenyl group. The terms Z; $R^1$; $R^2$; $R^3$; $R^4$; and $R^8$ refer to the terms as defined in this application.

In (a) of the synthetic scheme, a thiourea compound (II) is reacted with a an ester, e.g. a cyanoacetate ester such as ethyl cyanoacetate to cause cyclization to a uracil compound (III), for example as depicted below:

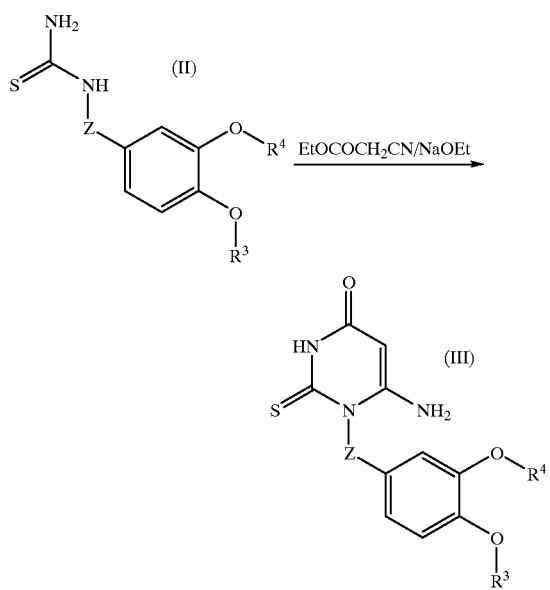

The cyclization reaction preferably occurs from about 80° C. to about 120° C., although other temperature ranges can be used e.g. from about 60° C. to about 150° C., and may occur in the presence of an alcohol solvent, e.g. isopropanol. Other reactants that are optionally present during the cyclization reaction include a base, e.g. sodium or potassium alkoxide, or other alkali metal salts (e.g. calcium sulfate, sodium chloride, potassium sulfate, sodium carbonate, lithium chloride, tripotassium phosphate, sodium borate, potassium bromide, potassium fluoride, sodium bicarbonate, calcium chloride, magnesium chloride, sodium citrate, sodium acetate, calcium lactate, magnesium sulfate and sodium fluoride). An exemplary alkoxide is sodium ethoxide.

Step (b) of the reaction comprises the elaboration of compound (III) to a corresponding amide (IV). The second step comprises successive amination, reduction, and amidation reactions, for example as depicted below.

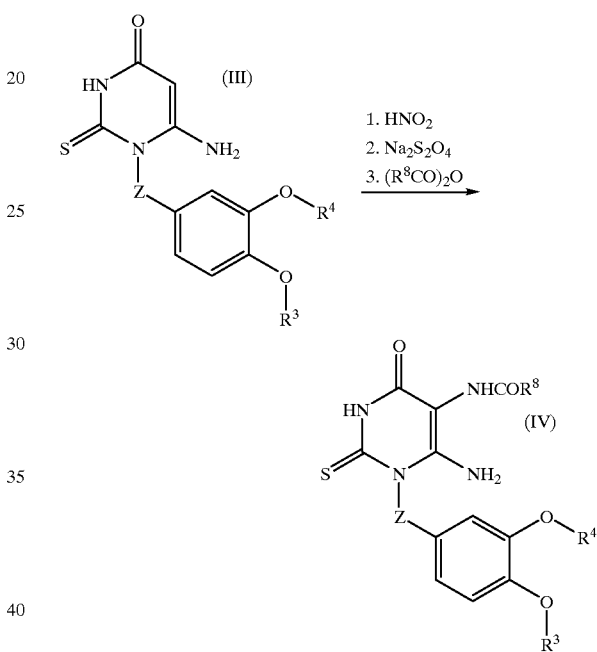

In the aminating reaction of sub-step of step (b), the reaction may occur in the presence of a nitrosating reagent formed from mineral acid, e.g. phosphoric acid, and a nitrite salt, e.g. sodium nitrite. The reaction may occur in the presence of a common organic solvent, such as DMSO or THF, at a preferable temperature range of from about 30° C. to about 60° C., although other temperature ranges can be use, e.g. from about 0° C. to about 60° C.

Thereafter, reduction takes place with sodium or potassium dithionite, in the presence of an alcohol or water solvent, at a preferable temperature range from about 0° C. to about 30° C., although other temperature ranges can be used. Alternatively, instead of sodium or potassium dithionite, the reduction step may comprise numerous other reducing agents or methods of reduction known to persons of ordinary skill in the art. Exemplary alternative reducing agents include for example Raney Nickel, and alternative methods of reduction are reduction by catalytic hydrogenation or by hydride reduction.

The amidation reaction of step (b) may occur with an acid anhydride or acid chloride in the presence of a base, such as triethylamine. The reaction may occur at from about 10° C. to about 30° C., preferably from 0–5° C., in the presence of a suitable solvent, e.g. THF and/or water.

Step (c) of the synthetic scheme of the invention comprises cyclization of compound (IV) to a corresponding xanthine compound (V). The cyclization reaction may occur in the presence of a base, e.g. sodium or potassium hydroxide, or a non-nucleophilic alternative such as sapotassium t-butoxide. Depicted below is an example of step(c):

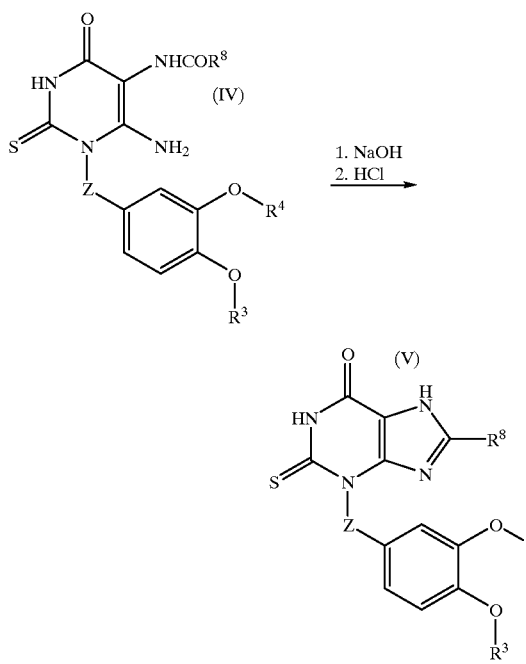

The reaction preferably occurs from about 60° C. to about 100° C., although other temperature ranges may be used, e.g. from about 40° C. to about 120° C., in the presence of an alcohol solvent, such as isopropanol. Following ring closure, the reaction is neutralized and the product is isolated in a neutral form.

Step (d) of the synthetic scheme of the invention, compound (V) is reacted with a suitable desulfurization compound, e.g. raney nickel or a nickel aluminum alloy, to form compound (IV), for example as shown below:

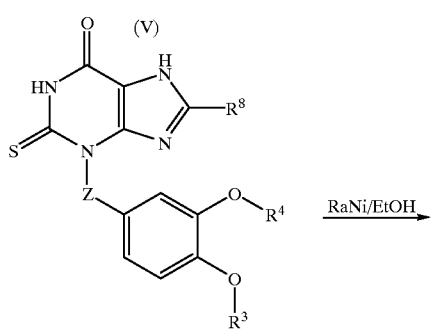

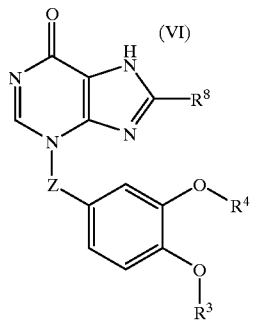

The desulfuration reaction occurs at from about 60° C. to about 100° C., in the presence of a suitable alcoholic solvent, such as ethanol or 1-propanol.

After the desulfuration, step (e) of the synthetic scheme of the invention involves the 6-oxo group of the resulting hypoxanthine (VI) being transformed to the amine by successive halogenation, e.g. chlorination, and displacement to give an adenine compound (I) of the invention, for example as shown below:

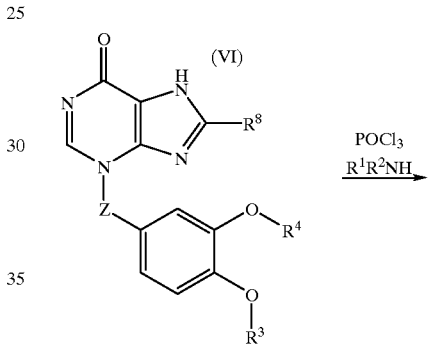

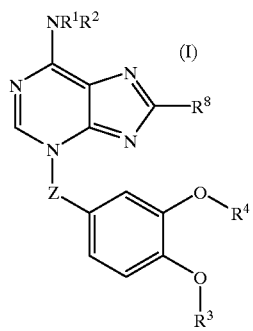

The halogenation step preferably occurs at a temperature range from about 40° C. to about 80° C., although other temperature ranges can be used, e.g. from about 20° C. to about 100° C. The reaction may occur in a toluene or other hydrocarbon solvent, for example dichloromethane or chloroform. The halogenating agent is preferably a chlorinating reagent e.g. phosphorous oxychloride, thionyl chloride or oxalyl chloride. The adenine formation occurs in a reaction with an amine in an alcoholic or aqueous solution, at a preferable temperature range from about 0° C. to about 30° C., although other temperature ranges can be used, e.g. from about 0° C. to about 60° C.

While the invention has been illustrated with respect to the production and use of particular compounds, it is appar-

Having thus described the invention, what is claimed is:

1. A method of forming a compound having the formula (I):

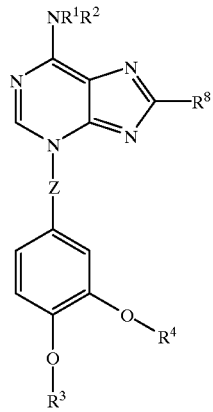

wherein:

Z is selected from the group consisting of $CH_2$, $CH_2CH_2$, $CH(CH_3)$, $CH=CH$, $C\equiv C$, NH, $N(C_1-C_3$ alkyl), O, S, $C(O)CH_2$ and $OCH_2$;

$R^1$ and $R^2$ are independently selected from the group consisting of hydrogen and a $C_1-C_8$ straight or branched alkyl or a $C_3-C_8$ cycloalkyl;

$R^3$ is a $C_1-C_{12}$ straight or branched alkyl;

$R^4$ is a $C_3-C_{10}$ cycloalkyl optionally substituted with OH, or a $C_3-C_{10}$ cycloalkenyl optionally substituted with OH; and $R^8$ is a $C_1-C_8$ straight or branched alkyl or a $C_3-C_8$ cycloalkyl, optionally substituted with OH;

said method comprising the steps of;

(a) reacting a compound of the formula (II)

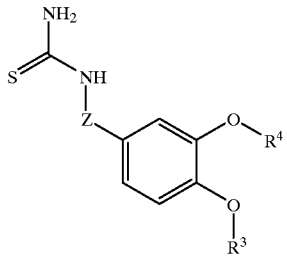

wherein Z, $R^3$ and $R^4$ are as defined above, with an effective amount of ethyl cyanoacetate to form a compound of the formula (III)

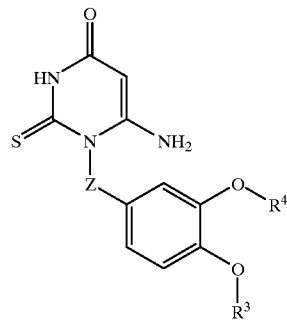

wherein Z, $R^3$ and $R^4$ are as defined above;

(b) subjecting said compound (III) to successive steps of nitrosating with a nitrosating agent to form a nitro group, reduction of the nitro group to an amine group with a reducing agent, and acylation of the amine group to an amide group with an acylating agent, to form compound (IV)

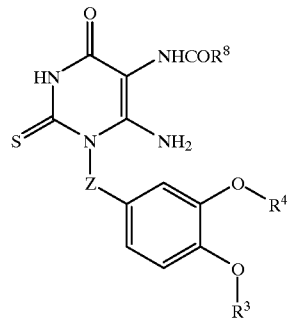

wherein Z, $R^3$, $R^4$ and $R^8$ are as defined above;

(c) reacting said compound (IV) with an effective amount of a base to form compound (V)

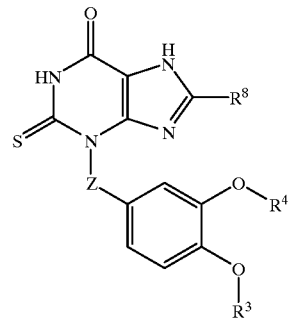

wherein Z, $R^3$, $R^4$ and $R^8$ are as defined above;

(d) reacting said compound (V) with an effective amount of a desulfurization compound to form compound (VI)

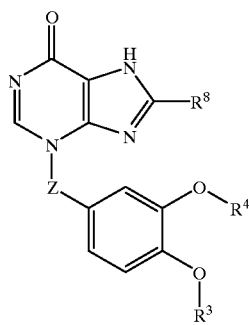

(VI)

wherein Z, R$^3$, R$^4$ and R$^8$ are as defined above; and (e) subjecting said oxo group of compound (VI) to the successive steps of halogenation with a halogenating agent and displacement with an amine of the formula NR$^1$R$^2$, wherein R$^1$ and R$^2$ are as defined above, to form said compound of formula 1.

2. The method of claim 1 wherein R$^4$ is cyclopentyl.
3. The method of claim 2 wherein R$^3$ is methyl.
4. The method of claim 3 where Z is CH$_2$.
5. The method of claim 1, wherein said halogenating agent of step (e) is selected from the group consisting of phosphorous chloride, thionyl chloride and oxalyl chloride.
6. The method of claim 1, wherein said acylation step occurs in the presence of a base.
7. The method of claim 1, wherein said step (a) occurs in the presence of sodium ethoxide.
8. The method of claim 1, wherein said nitrosating agent of said step (b) is formed from a mineral acid and a nitrite salt.
9. The method of claim 8, wherein said mineral acid is phosphoric acid.
10. The method of claim 1, wherein said reduction of said step (b) occurs in the presence of sodium dithionate or potassium dithionite.
11. The method of claim 1, wherein said acylation agent of said step (b) is an acid anhydride or acid chloride.
12. The method of claim 1, wherein said step (c) occurs in the presence of a base.
13. The method of claim 12, wherein said base is selected from the group consisting of sodium hydroxide or potassium hydroxide.
14. The method of claim 1, wherein said desulfurization compound of step (d) is Raney Nickel.
15. The method of claim 8, wherein said nitrite salt is sodium nitrite.

* * * * *